United States Patent
Barimani et al.

(10) Patent No.: US 11,232,861 B1
(45) Date of Patent: Jan. 25, 2022

(54) SYSTEMS AND METHODS FOR DISPLAYING PREDETERMINED INFORMATION FOR CLINICAL USE

(71) Applicants: Bardia Barimani, Montreal (CA); Vic Caruso, Montreal (CA); Adam Hart, Montreal (CA); Carl Laverdiere, Montreal (CA); Michael Tanzer, Montreal (CA); Robert Young, Montreal (CA)

(72) Inventors: Bardia Barimani, Montreal (CA); Vic Caruso, Montreal (CA); Adam Hart, Montreal (CA); Carl Laverdiere, Montreal (CA); Michael Tanzer, Montreal (CA); Robert Young, Montreal (CA)

(73) Assignee: ARGOS HEALTH INC., Outremont (CA)

(*) Notice: Subject to any disclaimer, the term of this patent is extended or adjusted under 35 U.S.C. 154(b) by 0 days.

(21) Appl. No.: 17/351,938

(22) Filed: Jun. 18, 2021

(51) Int. Cl.
*G16H 40/20* (2018.01)
*G06K 7/10* (2006.01)
*G16H 20/40* (2018.01)

(52) U.S. Cl.
CPC ......... *G16H 40/20* (2018.01); *G06K 7/10366* (2013.01); *G16H 20/40* (2018.01)

(58) Field of Classification Search
CPC ..... G16H 40/20; G16H 20/40; G06K 7/10366
See application file for complete search history.

(56) References Cited

U.S. PATENT DOCUMENTS

| | | | |
|---|---|---|---|
| 9,498,231 B2* | 11/2016 | Haider | A61B 5/1076 |
| 2014/0263633 A1* | 9/2014 | Schmucker | G06Q 10/0875 |
| | | | 235/385 |
| 2017/0098049 A1* | 4/2017 | Sweeney | G16H 40/20 |
| 2020/0008881 A1* | 1/2020 | Marti | A61B 34/20 |

* cited by examiner

*Primary Examiner* — Toan N Pham
(74) *Attorney, Agent, or Firm* — BCF LLP

(57) ABSTRACT

Systems and methods for display of information for clinical use. The method is executable by a processor of a computer system and comprises: (i) receiving data, by the processor, from a communication network comprising: a first reader, a second reader and a wireless sensor network (WSN) router, (ii) based on the received data, determining at least one of a position and an orientation of a given element of the plurality of elements, (iii) in response to the determined at least one of the position and the orientation, causing to be displayed, on a display communicatively coupled to the computer system, predetermined information associated with the determined at least one of a position and an orientation.

20 Claims, 8 Drawing Sheets

SYSTEMS AND METHODS FOR DISPLAYING PREDETERMINED INFORMATION FOR CLINICAL USE

CROSS-REFERENCE TO RELATED APPLICATIONS

This is the first application filed for the instantly disclosed technology.

TECHNICAL FIELD

The present disclosure generally relates to computer implemented methods and systems for causing a display of information for clinical use, and particularly, although not exclusively, wherein the display is an augmented reality or a mixed reality based virtual display overlaid on a real environment.

BACKGROUND

Typically, in clinical environments such as operating rooms (ORs), one or more users (e.g., clinician, surgeon, surgical assistant, nurse, patient, trainee clinician, etc.) must refer to many different types of visual patient information during a medical procedure. Visual patient information may include images and videos of the patient or body parts of the patient acquired by imaging equipment, such as one or more of magnetic resonance imaging equipment, computed tomography scanning equipment, x-ray equipment, three-dimensional (3D) ultrasound equipment, endoscopic equipment, 3D computer modeling equipment, patient monitoring equipment. Visual patient information may also include test results, such as those printed on paper, or displayed on a screen as retrieved from a medical records database. As well, visual information may also include procedure-related information, such as those printed on paper, or displayed on a screen as retrieved from surgical/medical technique protocol database The visual patient information assists the one or more user (such as the surgeon and the surgical assistant) to plan for and execute the medical procedure.

ORs therefore typically include many displays positioned at various locations for displaying the visual patient information during the medical procedure to the users. For example, there may be one or more displays hung from a ceiling, mounted on a wall, and/or supported on a cart of the OR. However, positioning all the displays for convenient viewing by all necessary users at all time points during the medical procedure is difficult, if not impossible. Furthermore, the necessity, for a single user, to frequently shift their focal reference between remotely located multiple displays as well as the patient often can cause fatigue in that user and have a deleterious effect on quality of the procedure. Moreover, a given display of the patient information may require mental translation between an orientation of an anatomy of the patient information shown on the display and the orientation of the actual anatomy of the patient can be particularly difficult, prone to errors, or inefficiently time-consuming for the users during the medical procedure.

Finally, locating the precise location on the patient from the patient information on the display can also be difficult. For example, it can be difficult for the user to identify where a particular location within a displayed x-ray or other image corresponds to on the patient. Moreover, the user may have used a 3D anatomical model to practice before the medical procedure, but may not be able to effectively use the model during the medical procedure because of the inherent difficulty of relating the model to the patient in real-time.

It is desired to provide alternative and/or improved methods and systems for causing display of information for clinical use.

SUMMARY

The embodiments of the present disclosure have been developed based on Developers' appreciation of shortcomings associated with the prior art. Developers have noted that augmented reality and mixed reality methods and systems exist to overlay patient information over the real environment during a medical procedure or in a clinical setting. Such virtual display methods and systems can obviate some of the problems noted above such as the need to view different displays in different locations. The augmented reality and/or mixed reality methods and systems of the prior art utilize markers attached to an object, such as the patient, a medical instrument or the user, to track a movement of the object. The tracked movement is then used as a trigger for the display of information on a display associated with the user.

However, Developers have noted that such prior art systems using virtual display overlays suffer from lack of sufficient accuracy, stability and reliability as they use conventional communication techniques to transmit data from various markers to a computer system which receives data from the markers, tracks their movement and causes the virtual display.

In particular, Developers have noted that the conventional communication techniques rely on a single communication route for data transmission from the markers to the computer system. In an event of disruption of the communication route, the conventional communication techniques may encounter several operational failures. During a medical/surgical procedure, this can have catastrophic if not fatal outcomes.

To overcome such shortcomings, Developers of the present technology have devised systems and methods for displaying information for clinical use using augmented reality or mixed reality technologies, for example, and which rely on more than one communication route between markers and a computer system.

The systems and methods of the present technology comprise multiple elements (markers) which can transmit data to a computer system through at least two communication routes, and in some embodiments, through three or four communication routes. Data transmission through multiple routes therefore can provide back-up in case one communication route is disrupted, thereby ensuring a reliable communication link.

In embodiments of the present technology, different communication routes are broadly provided by utilizing more than one reader, each configured to receive data from each element. In other words, embodiments of the present technology rely on at least two readers, such as a first reader and a second reader, that independently communicate with the plurality of elements to receive the data and to directly communicate the data via a communication link to the computer system. In addition, in certain non-limiting embodiments, the first reader and the second reader may be configured to wirelessly communicate with the computer system via a wireless sensor network (WSN) router.

Thus, providing more than one reader, such as the first reader and the second reader, instead of a single reader, and optionally an additional communication layer of the WSN router may provide multiple copies of the data from the elements to the computer system for processing and thereby ensure a more accurate, stable and reliable system.

In accordance with the first broad aspect of the present disclosure, there is provided a method for displaying information for clinical use, the method executable by a processor of a computer system, the method comprising: receiving data, by the processor, from a communication network comprising: a first reader, a second reader and a wireless sensor network (WSN) router: the first reader being communicatively coupled to, and configured to receive data from, each element of a plurality of elements, each element positioned at a given location relative to an object at a clinical site; the second reader being communicatively coupled to, and configured to receive data from, each element of the plurality of elements; the WSN router communicatively coupled to, and configured to receive data from, each of the first reader and the second reader; based on the received data, determining at least one of a position and an orientation of a given element of the plurality of elements; in response to the determined at least one of the position and the orientation, causing to be displayed, on a display communicatively coupled to the computer system, predetermined information associated with the determined at least one of a position and an orientation.

In accordance with certain embodiments of the present disclosure, the method further comprises: determining if the data has been received from more than one of: the first reader, the second reader and the WSN router; in response to the data having been received from more than one of the first reader, the second reader and the WSN router, filtering the data to obtain filtered data, the filtering comprising disregarding duplicate data based on a predetermined rule, the determining the at least one of the position and the orientation being based on the filtered data.

In accordance with certain embodiments of the present disclosure, the predetermined rule comprises one of: a predetermined hierarchy of communication routes between the plurality of elements and the computer system, a predetermined hierarchy of time of transmission of the data; and a predetermined hierarchy of time of reception of the data by the computer system.

In accordance with certain embodiments of the present disclosure, the object is one or more of: a patient, a medical/surgical instrument, and operating/procedural table.

In accordance with certain embodiments of the present disclosure, determining at least one of the position and the orientation of the given element of the plurality of elements comprises triangulation.

In accordance with certain embodiments the present disclosure, triangulation is performed by computing angles of incidences between the plurality of elements and the first reader and the second reader.

In accordance with certain embodiments of the present disclosure, at least one of the position and the orientation of the given element of the plurality of elements is determined based on a 3D point cloud representation of region of interest (ROI).

In accordance with certain embodiments of the present disclosure, the display is a fixed display or is part of a wearable device. The wearable device may include but not be limited to a headset, glasses or contact lenses. The display may be configured to project a holographic projection.

In accordance with certain embodiments of the present disclosure, the predetermined information is one or more of: an augmented image, a medical/surgical procedure guidance, a navigation menu, an eye fatigue indicator, a user's profile, and an annotation.

In accordance with certain embodiments of the present disclosure, the displayed information comprises an actionable digital element, based on an input received from a user, the actionable digital element is configured to display of further information associated with the predetermined information.

In accordance with certain embodiments of the present disclosure, the processor is configured to retrieve the predetermined information from a memory of the computer system.

In accordance with certain embodiments of the present disclosure, the predetermined information which is displayed is based on a user's profile.

In accordance with certain embodiments of the present disclosure, the displayed information comprises a virtual display created by an augmented reality or a mixed reality method.

In accordance with certain embodiments of the present disclosure, determining if the data was received from more than one of the first reader, the second reader and the WSN router comprises the processor interrogating the first reader, the second reader and the wireless sensor network (WSN) router to determine if any one of communication routes between the plurality of elements and the computer system was compromised.

In accordance with certain embodiments of the present disclosure, the communication network defines a plurality of communication routes between each of the plurality of elements and the computer system. In certain embodiments, the communication routes include: (i) between each of the plurality of elements, the first reader and the computer system, (ii) between each of the plurality of elements, the second reader, and the computer system, (iii) between each of the plurality of elements, the first reader, the WSN router, and the computer system, and (iv) between each of the plurality of elements, the second reader, the WSN router, and the computer system.

In accordance with certain embodiments of the present disclosure, the method further comprises tracking user's eye, head or arm movement for interaction with the display.

In accordance with certain embodiments of the present disclosure, the at least some of the plurality of elements are radio frequency based elements. In certain embodiments, all of the plurality of elements are radio frequency based elements.

In accordance with certain embodiments of the present disclosure, at least some of the plurality of elements are optical based elements.

In accordance with a second broad aspect of the present disclosure, there is provided a system for generating a display of information for clinical use, the system comprising a communication network including: a plurality of elements having data stored therein and positioned at a given location relative to an object at a clinical site; a first reader and a second reader, each of the first reader and the second reader communicatively coupled to each element of the plurality of elements and configured to receive the data from each element of the plurality of elements and transmit the data to a computer system; a wireless sensor network (WSN) router configured to receive the data from the first reader and the second reader and transmit the data to the computer system; the computer system being independently communicatively coupleable with each of the first reader, the second reader and the WSN router for receiving the transmitted data independently from each of the first reader, the second reader and the WSN router; wherein the computer system is configured to execute a method comprising: receiving data from the communication network; based on the received data, determining at least one of a position and an orientation of a given element of the plurality of elements; in response to the at least one of the determined position and the orientation, causing display, on a display communicatively coupled to the computer system, predetermined information associated with the determined the at least one of a determined position and an orientation.

In accordance with certain embodiments of the present disclosure, the at least some of the plurality of elements are radio frequency based elements.

In accordance with certain embodiments of the present disclosure, at least some of the plurality of elements are optical based elements.

In accordance with certain embodiments of the present disclosure, the display is incorporated in a wearable device that includes, but is not limited to headgear, glasses or contact lenses, or the display is a fixed display associated with an electronic device such as mobile device. The display may be configured to project a holographic projection.

In accordance with a third broad aspect of the present disclosure, there is provided a method for displaying information for clinical use, the method executable by a processor of a computer system, the method comprising: receiving data, by the processor, from a communication network comprising: a first reader and a second reader: the first reader being communicatively coupled to, and configured to receive data from, each element of a plurality of elements, each element positioned at a given location relative to an object at a clinical site; the second reader being communicatively coupled to, and configured to receive data from, each element of the plurality of elements, each element positioned at a given location relative to an object at a clinical site; determining, by the processor, if the data has been received from one or more of the first reader and the second reader; in response to the data having been received from more than one of the first reader and the second reader, filtering the data to obtain filtered data, the filtering comprising disregarding duplicate data; determining, based on the filtered data, at least one of a position and an orientation of a given element of the plurality of elements; in response to the determined at least one of the position and the orientation, cause to be displayed, on a display communicatively coupled to the computer system, predetermined information associated with the determined at least one of the position and the orientation.

In accordance with certain embodiments of the present disclosure, the communication network further comprises a wireless sensor network (WSN) router, the WSN router communicatively coupled to, and configured to receive data from, each of the first reader and the second reader, the method further comprising receiving data from the WSN router.

In accordance with certain embodiments of the present disclosure, the method further comprises: determining if the data has been received from more than one of: the first reader, and the second reader; in response to the data having been received from more than one of the first reader and the second reader, filtering the data to obtain filtered data, the filtering comprising disregarding duplicate data based on a predetermined rule, the determining the at least one of the position and the orientation being based on the filtered data.

In accordance with certain embodiments of the present disclosure, the predetermined rule comprises one of: a predetermined hierarchy of communication routes between the plurality of elements and the computer system, a predetermined hierarchy of time of transmission of the data; and a predetermined hierarchy of time of reception of the data by the computer system.

In accordance with certain embodiments of the present disclosure, the object is one or more of: a patient, a medical/surgical instrument, and an operating/procedural table.

In accordance with certain embodiments of the present disclosure, determining at least one of the position and the orientation of the given element of the plurality of elements comprises triangulation.

In accordance with certain embodiments the present disclosure, triangulation is performed by computing angles of incidences between the plurality of elements and the first reader and the second reader.

In accordance with certain embodiments of the present disclosure, at least one of the position and the orientation of the given element of the plurality of elements is determined based on a 3D point cloud representation of region of interest (ROI).

In accordance with certain embodiments of the present disclosure, the display is a fixed display or is part of a wearable device. The wearable device may include, but is not limited to be a headset, glasses or contact lenses. The display may be configured to project a holographic projection.

In accordance with certain embodiments of the present disclosure, the predetermined information is one or more of: an augmented/virtual image, a medical/surgical procedure guidance, a navigation menu, an eye fatigue indicator, a user's profile, and an annotation.

In accordance with certain embodiments of the present disclosure, the displayed information comprises an actionable digital element, based on an input received from a user, the actionable digital element is configured to display further information associated with the predetermined information.

In accordance with certain embodiments of the present disclosure, the processor is configured to retrieve the predetermined information from a memory of the computer system.

In accordance with certain embodiments of the present disclosure, the predetermined information which is displayed is based on a user's profile.

In accordance with certain embodiments of the present disclosure, the displayed information comprises a virtual display created by an augmented reality or a mixed reality method.

In accordance with certain embodiments of the present disclosure, determining if the data was received from more than one of the first reader and the second reader comprises the processor interrogating the first reader and the second reader to determine if any one of communication routes between each of the plurality of elements and the computer system was compromised.

In accordance with certain embodiments of the present disclosure, the communication network defines a plurality of communication routes between the plurality of elements and the computer system. In certain embodiments, the communication routes include: (i) between each of the plurality of elements, the first reader and the computer system, and (ii) between each of the plurality of elements, the second reader, and the computer system.

In accordance with certain embodiments of the present disclosure, the method further comprises tracking user's eye, head or arm movement for interaction with the display.

In accordance with certain embodiments of the present disclosure, the at least some of the plurality of elements are radio frequency based elements. In certain embodiments, all of the plurality of elements are radio frequency based elements.

In accordance with certain embodiments of the present disclosure, at least some of the plurality of elements are optical based elements.

In accordance with a fourth broad aspect of the present disclosure, there is provided a system for generating a display of information for clinical use, the system comprising a communication network including: a plurality of elements having data stored therein and positioned at a given location relative to an object at a clinical site; a first reader and a second reader, each of the first reader and the second reader communicatively coupled to each element of the plurality of elements and configured to receive the data from each element of the plurality of elements and transmit the data to a computer system; the computer system being independently communicatively coupleable with each of the first reader, and the second reader for receiving the transmitted data independently from each of the first reader and the second reader; wherein the computer system is configured to execute a method comprising: receiving data from the communication network; based on the received data, determining at least one of a position and an orientation of a given element of the plurality of elements; in response to the at least one of the determined position and the orientation, causing display, on a display communicatively coupled to the computer system, predetermined information associated with the determined the at least one of a determined position and an orientation.

In accordance with certain embodiments of the present disclosure, the at least some of the plurality of elements are radio frequency based elements.

In accordance with certain embodiments of the present disclosure, at least some of the plurality of elements are optical based elements.

In accordance with certain embodiments of the present disclosure, the display is incorporated in a wearable device such as, but not limited to a headgear, glasses or contact lenses, or the display is a fixed display associated with an electronic device such as mobile device. The fixed display may include but not limited to holographic projection.

Unless otherwise defined or indicated by context, all technical and scientific terms used herein have the same meaning as commonly understood by one of ordinary skill in the art to which the described embodiments appertain to.

In the context of the present specification, "computer system" is any computer hardware that is capable of running software appropriate to the relevant task at hand. In the context of the present specification, in general the term "computer system" is associated with a user of the computer system. Thus, some (non-limiting) examples of computer systems include personal computers (desktops, laptops, netbooks, etc.), smartphones, and tablets, as well as network equipment such as routers, switches, and gateways. It should be noted that a device acting as a computer system in the present context is not precluded from acting as a server to other computer systems. The use of the expression "a computer system" does not preclude multiple computer systems being used in receiving/sending, carrying out or causing to be carried out any task or request, or the consequences of any task or request, or steps of any method described herein.

In the context of the present disclosure, the expression "data" includes data of any nature or kind whatsoever capable of being stored in a database. Thus, data includes, but is not limited to, audiovisual works (images, movies, sound records, presentations etc.), data (location data, numerical data, etc.), text (opinions, comments, questions, messages, etc.), documents, spreadsheets, etc.

In the context of the present disclosure, unless expressly indicated otherwise, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present disclosure, "communication/communicate" between two nodes, a node and a processor/controller, a node and a server, a pipeline and a server, any two modules, any two software components, or any two hardware components, refers to as the exchange, transfer, sending, receiving, sharing or the like of information, request, data, or the like without limiting the scope of present disclosure.

Software modules, modules, or units which are implied to be software, may be represented herein as any combination of flowchart elements or other elements indicating performance of process steps and/or textual description. Such modules may be executed by hardware that is expressly or implicitly shown.

In the context of the present specification, unless provided expressly otherwise, the words "first", "second", "third", etc. have been used as adjectives only for the purpose of allowing for distinction between the nouns that they modify from one another, and not for the purpose of describing any particular relationship between those nouns. Thus, for example, it should be understood that, the use of the terms "first processor" and "third processor" is not intended to imply any particular order, type, chronology, hierarchy or ranking (for example) of/between the server, nor is their use (by itself) intended to imply that any "second server" must necessarily exist in any given situation. Further, as is discussed herein in other contexts, reference to a "first" element and a "second" element does not preclude the two elements from being the same actual real-world element. Thus, for example, in some instances, a "first" server and a "second" server may be the same software and/or hardware, in other cases they may be different software and/or hardware.

It will be understood that when an element is referred to as being "connected" or "coupled" to another element, it can be directly or indirectly connected or coupled to the other element or intervening elements that may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

In the context of the present specification, when an element is referred to as being "associated with" another element, in certain embodiments, the two elements can be directly or indirectly linked, related, connected, coupled, the second element employs the first element, or the like without limiting the scope of present disclosure.

The terminology used herein is only intended to describe particular representative embodiments and is not intended to be limiting of the present technology. As used herein, the singular forms "a" "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Implementations of the present technology each have at least one of the above-mentioned objects and/or aspects, but do not necessarily have all of them. It should be understood that some aspects of the present technology that have resulted from attempting to attain the above-mentioned object may not satisfy this object and/or may satisfy other objects not specifically recited herein,

BRIEF DESCRIPTION OF THE FIGURES

Further features and advantages of the present disclosure will become apparent from the following detailed description, taken in combination with the appended drawings, in which.

Figure 1:
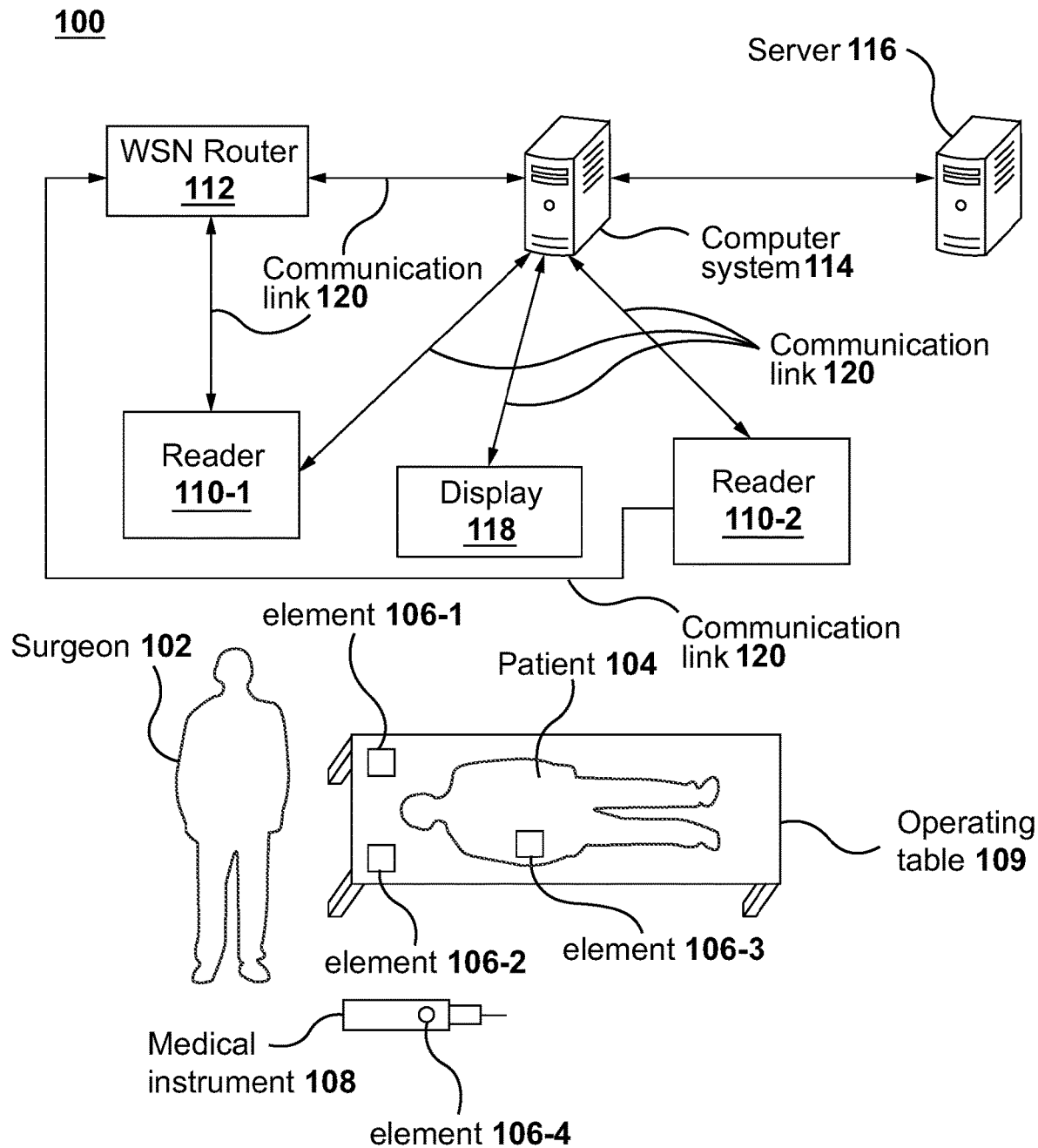
FIG. 1 illustrates a system for generating display of information for clinical use, in accordance with various non-limiting embodiments of the present disclosure.

It is to be understood that throughout the appended drawings and corresponding descriptions, like features are identified by like reference characters. Furthermore, it is also to be understood that the drawings and ensuing descriptions are intended for illustrative purposes only and that such disclosures do not provide a limitation on the scope of the claims.

DETAILED DESCRIPTION

The instant disclosure is directed to addressing at least some of the deficiencies of the prior art. In particular, described herein is a system and method for generating a display of information for clinical use, using for example augmented reality and/or mixed reality technologies and which is reliant on more than one communication route between elements associated with objects in a clinical setting and a computer system from receiving data from the elements.

The examples and conditional language recited herein are principally intended to aid the reader in understanding the principles of the present technology and not to limit its scope to such specifically recited examples and conditions. It will be appreciated that those skilled in the art may devise various arrangements which, although not explicitly described or shown herein, nonetheless embody the principles of the present technology and are included within its spirit and scope.

Furthermore, as an aid to understanding, the following description may describe relatively simplified implementations of the present technology. As persons skilled in the art would understand, various implementations of the present technology may be of a greater complexity.

In some cases, what are believed to be helpful examples of modifications to the present technology may also be set forth. This is done merely as an aid to understanding, and, again, not to define the scope or set forth the bounds of the present technology. These modifications are not an exhaustive list, and a person skilled in the art may make other modifications while nonetheless remaining within the scope of the present technology. Further, where no examples of modifications have been set forth, it should not be interpreted that no modifications are possible and/or that what is described is the sole manner of implementing that element of the present technology.

Moreover, all statements herein reciting principles, aspects, and implementations of the present technology, as well as specific examples thereof, are intended to encompass both structural and functional equivalents thereof, whether they are currently known or developed in the future. Thus, for example, it will be appreciated by those skilled in the art that any block diagrams herein represent conceptual views of illustrative circuitry embodying the principles of the present technology. Similarly, it will be appreciated that any flowcharts, flow diagrams, state transition diagrams, pseudo-code, and the like represent various processes which may be substantially represented in computer-readable media and so executed by a computer or processor, whether or not such computer or processor is explicitly shown.

The functions of the various elements shown in the figures, including any functional block labeled as a "processor" or a "processing unit", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. In some embodiments of the present technology, the processor may be a general-purpose processor, such as a central processing unit (CPU) or a processor dedicated to a specific purpose, such as a graphics processing unit (GPU). Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read-only memory (ROM) for storing software, random access memory (RAM), and non-volatile storage. Other hardware, conventional and/or custom, may also be included.

With these fundamentals in place, and as stated earlier, the instant disclosure is directed to systems and methods for generating the display of information for clinical use and which may use augmented reality (AR) and/or mixed reality (MR) technologies to create the displays of information.

MR is a technology used for merging of real and virtual worlds to produce new environments and visualizations, where physical and digital objects co-exist and interact in real time. Mixed reality does not exclusively take place in either the physical world or virtual world, but is a hybrid of reality and virtual reality.

In contrast, the AR technology takes place in the physical world, with information or objects added virtually. AR is technology is used for displaying virtual or "augmented" objects or visual effects overlaid on a real environment. The real environment may include a room or specific area or may be more general to include the world at large. The virtual aspects overlaid on the real environment may be represented as anchored or in a set position relative to one or more aspects of the real environment.

It is to be noted that the present technology is not particularly limited in the technology used to create the display of information, whether AR or MR. The present technology is directed to providing a reliable communication link between elements associated with the object and the computer system, regardless of whether AR, MR or other virtual technology is used to display the information.

Embodiments of the systems and methods herein will be described with reference to MR display of virtual components or representations of real objects overlaid on a real environment and facilitating an interaction of a user with the virtual components. An MR based display allows the user (e.g., clinician, surgeon, surgical assistant, nurse, patient, trainee clinician, etc.) to view and interact with the displayed virtual objects that appear to be projected into the real environment, the real environment also being visible to the user. In one non-limiting embodiment, the MR based display typically includes two or more display lenses or screens, including one for each eye of the user. The two display lenses or screens are configured to transmit light such that the real environment is visible to the user while also projecting the virtual components or representations of the real objects overlaid to make visible to the user of the MR based display.

The two or more MR based displays may be used in a coordinated manner, for example with a first MR based display controlling one or more additional MR based displays, or in a system with defined roles. For example, when activating an MR based display, the user may select a role (e.g., surgeon, surgical assistant, nurse, patient, trainee clinician, etc.) during a surgical procedure or other event and the MR based display may illustrate information (also referred to herein as "predetermined information") relevant to that role. In other examples, the user may select a specific event for which the MR display is required, such as surgery, therapy, training, patient consultation. The specific events or the specific roles are not particularly limited and embodiments of the present technology can be applied to a broad range of roles and events. The information may comprise predetermined information relevant either to the selected event or to a predetermined time within that event. In this respect, the predetermined information may comprises a sequence of predetermined information modules.

FIG. 1 illustrates a system 100 for generating the MR display of information for clinical use, in accordance with various non-limiting embodiments of the present disclosure. As shown, the system 100 may include a plurality of elements 106-1, 106-2, 106-3, and 106-4, readers 110-1 and 110-2, a wireless sensor network (WSN) router 112, a computer system 114, and a display 118. Optionally, the system 100 may include a server 116. The system 100 may include other components and modules, however such components have been omitted from FIG. 1 for the purpose of simplicity.

In certain non-limiting embodiments, the plurality of elements 106-1, 106-2, 106-3, and 106-4 may be configured to track one or more objects such as tracking a movement of a medical instrument 108, including but not limited to a scalpel, a clamp, a forcep, scissors, an osteotome, a retractor, leads, dissector, an implant, a filler, or tracking a movement of a patient 104 or a body part of the patient, such as an arm, a leg, a torso, and the like. In certain non-limiting embodiments, different medical/surgical instruments 108 to be tracked and/or tracked targets such as the patient 104 may be provided with a respective set of the plurality of elements 106-1, 106-2, 106-3, and 106-4 in different configurations.

In certain non-limiting embodiments, the plurality of elements 106-1, 106-2, 106-3, and 106-4 may be active or passive elements. For example, active elements may include infrared emitters for use with an optical sensor. Passive elements may include reflective spheres for use with the optical sensor, or pick-up coils for use with an electromagnetic reader, for example.

In certain non-limiting embodiments, the plurality of elements 106-1, 106-2, 106-3, and 106-4 may all be the same type or may include a combination of two or more different types of markers. In some non-limiting embodiments, the plurality of elements 106-1, 106-2, 106-3, and 106-4 may be radiofrequency (RF) based markers. In other non-limiting embodiments, the plurality of elements 106-1, 106-2, 106-3, and 106-4 may include but are not limited to reflective markers, electromagnetic (EM) markers, pulsed or un-pulsed light-emitting diode (LED) markers, glass markers, reflective adhesives, or reflective unique structures or patterns, among others.

It is to be noted that RF and EM markers may have specific signatures for the specific medical/surgical instrument 108 or the patient body part they may be attached to or otherwise associated with. Reflective adhesives, structures and patterns, glass markers, and LED markers may be detectable using optical sensors, while RF and EM markers may be detectable using RF readers and EM readers. Different marker types may be selected to suit different clinical conditions or other clinical needs. For example, using EM and RF markers may enable tracking of the medical instrument 108 without requiring a line-of-sight from the readers 110-1 and 110-2 to the plurality of elements 106-1, 106-2, 106-3, and 106-4, and using optical markers may avoid additional noise from electrical emission and detection systems In some examples, the plurality of elements 106-1, 106-2, 106-3, and 106-4 may include printed markers or 3D designs that may be used for detection by an auxiliary camera, such as a wide-field camera and/or the optical scope. Printed markers may also be used as a calibration pattern, for example to provide distance information (e.g., 3D distance information) to the optical sensor. Printed identification markers may include designs such as concentric circles with different ring spacing and/or different types of bar codes, among other designs.

In certain non-limiting embodiments, the plurality of elements 106-1, 106-2, 106-3, and 106-4 may have an associated data. In some of the plurality of elements 106-1, 106-2, 106-3, and 106-4, the associated data may be stored in a memory (in case of active elements). Also, in some of the plurality of elements 106-1, 106-2, 106-3, 106-4, the associated data may be embedded in the form of visual identification, such as bar codes (in case of passive elements).

In certain non-limiting, the readers 110-1 and 110-2 may be communicatively coupled to the plurality of elements 106-1, 106-2, 106-3, and 106-4 and configured to receive the associated data from each element of the plurality of elements 106-1, 106-2, 106-3, and 106-4. In certain non-limiting embodiments, the associated data may include but not be limited to previously assigned identifications (IDs), geographic locations, type of object (e.g., the medical/surgical instrument 108, the patient 104, the operating/procedural table 109 or the like) with which the plurality of elements 106-1, 106-2, 106-3, and 106-4 are associated with or any such data that may assist the computer system 114 to cause the information to be displayed on the display 118.

In certain non-limiting embodiments, the readers 110-1 and 110-2 may include RF readers. However, depending on type of the plurality of elements 106-1, 106-2, 106-3, and 106-4, the readers 110-1 and 110-2 may also include EM readers, optical scanners, optical sensors (e.g., a LIDAR or other depth sensor, infrared sensor, color camera, stereoscopic camera, thermographic camera, multispectral camera).

Further, in certain non-limiting embodiments, the plurality of elements 106-1, 106-2, 106-3, and 106-4 may be configured to communicate with the WSN router 112 and the computer system 114 via a communication link 120. The communication link 120 may be based on IEEE 802.11 family of standards or any other suitable standard.

Turning now to the display 118, in certain non-limiting embodiments, the display 118 may be a touch-sensitive screen for receiving touch inputs, part of a wearable device (e.g., MR glasses, MR lenses, or a MR headset), to provide the predetermined information as the MR based display, a fixed display for displaying still and/or video images (e.g., a live video image of the surgical field and/or 2D or 3D images obtained preoperatively) or any other suitable type of display. In certain non-limiting embodiments, the display may be configured to project interactive holographic projections.

The display 118 may include one or more lenses or screens, such as a single screen or two screens (e.g., one per eye of the user). The screens may allow light to be transmitted therethrough such that aspects of the real environment are visible while also displaying the predetermined information such that the predetermined information appears to be overlaid on the real environment.

The MR based display may be viewable to one or more users and may include differences among views available for the one or more viewers while retaining some aspects as universal among the views. For example, a heads-up display may change between two views while the predetermined information may be fixed to a real object or area in both views. Aspects, such as a color of an object, lighting, or other changes may be made among the views without changing a fixed position of at least one virtual object.

The display 118 may be used during a medical procedure, for example performed by a surgeon 102 on the patient 104. However, it is to be noted that in certain non-limiting embodiments, the surgeon 102 may be present at a remote location from the patient and may assist the medical procedure using robotic medical instruments (not illustrated). The display 118 may present the predetermined information, such as virtual objects, augmented still/video images, medical procedure guidance, navigation menu, eye fatigue indicator, surgeon's profile, annotations or the like, details of which will be discussed later in the disclosure, during the medical procedure to augment the surgeon's vision. The surgeon 102 may control the predetermined information using a remote controller for the display 118, by interacting with the display (e.g. when it is touch screen) or by interacting with the predetermined information (e.g., using a hand or a gesture to "interact" with the predetermined information). In another example, the predetermined information may be used as a guide for a path of the medical instrument 108 relative to the patient 104. In certain examples, the predetermined information may react to movements of other virtual or real-world objects in the surgical field. For example, the predetermined information may be altered when the surgeon 102 is manipulating the medical instrument 108 in proximity to the predetermined information.

The system 100 may be implemented in an environment where a medical procedure is to be implemented on a patient 104 by a surgeon 102 or other clinician. The medical/surgical procedures may include but are not limited to orthopaedic procedures, such as but not limited to, bone preparation, implant positioning, fracture management, osteotomies, limb lengthening, deformity correction, spine surgery, tumor resection, ligamentous reconstruction, osteoplasty, biopsy and decompression, rodding of long bones such as the femur, tibia and humerus, placement of screws or other fixation devices in percutaneously or in an open procedure, plate fixation and ring/external fixator placement or the like.

At least some of these medical/surgical procedures typically require pre- or intra-operative imaging guidance, such as fluoroscopic (x-ray) imaging, in order to achieve precise placement of the fixation device in a well-accepted location. This technology can simplify these procedures by displaying the ideal entry point and placement of the fixation devices as an AR or MR overlay over the anatomic/surgical site on the patient.

In one non-limiting example, the system 100 may assist the surgeon 102 in the fixation of an intertrochanteric hip fracture, which is commonly treated with a hip cephallomedullary nail. Correct position of the nail in the femur (thigh bone) and the lag screw placed in the femoral head directly correlates with success of the implant and patient outcomes. The optimal implant position is attained by inserting the nail via the correct entry point in the femur, and the subsequent ideal placement of the screw in the femoral head. To obtain the correct entry point and orientation, a wire has to be passed through the correct location on the femur. The system 100 may be utilized to predetermine the entry point of the guide wire and ensure accurate wire positioning and subsequent, nail and screw position.

It is to be noted that although the abovementioned medical procedures are related to orthopaedic procedures, the system 100 may be utilized in other medical/surgical procedures in which a virtual display of information relating to the procedure may be useful to the user of the system.

Developers have noted that certain MR techniques for displaying information to users during a medical procedure exist but rely on a single communication route to gather the data and provide the data to a computer system for further processing. In doing so, the conventional techniques may encounter various issues such as reduction or lack of accuracy, stability and reliability in case of interruption in the single communication route. This can have dangerous and potentially fatal outcomes. To this end, Developers have developed systems and methods that can reduce or overcome the problems associated with the conventional techniques.

To improve the shortcomings of the conventional techniques, in various non-limiting embodiments of the present disclosure, the system 100 may comprise a communication network with multiple communication routes. More specifically, the communication network may include at least two readers 110-1 and 110-2 that independently communicate with the plurality of elements 106-1, 106-2, 106-3, and 106-4 to gather the data. The readers 110-1 and 110-2 may be configured to directly communicate using the communication link 120 with the computer system 114 to provide the gathered data. In addition, in certain non-limiting embodiments, the readers 110-1 and 110-2 may be configured to wirelessly communicate with the computer system 114 via the WSN router 112. Thus, the communication network comprising at least two readers 110-1 and 110-2 in place of one and an additional communication layer of the WSN router 120 may provide multiple copies of the gathered data to the computer system 114 for processing and thereby ensuring a more accurate, stable and reliable system.

Figure 2A:
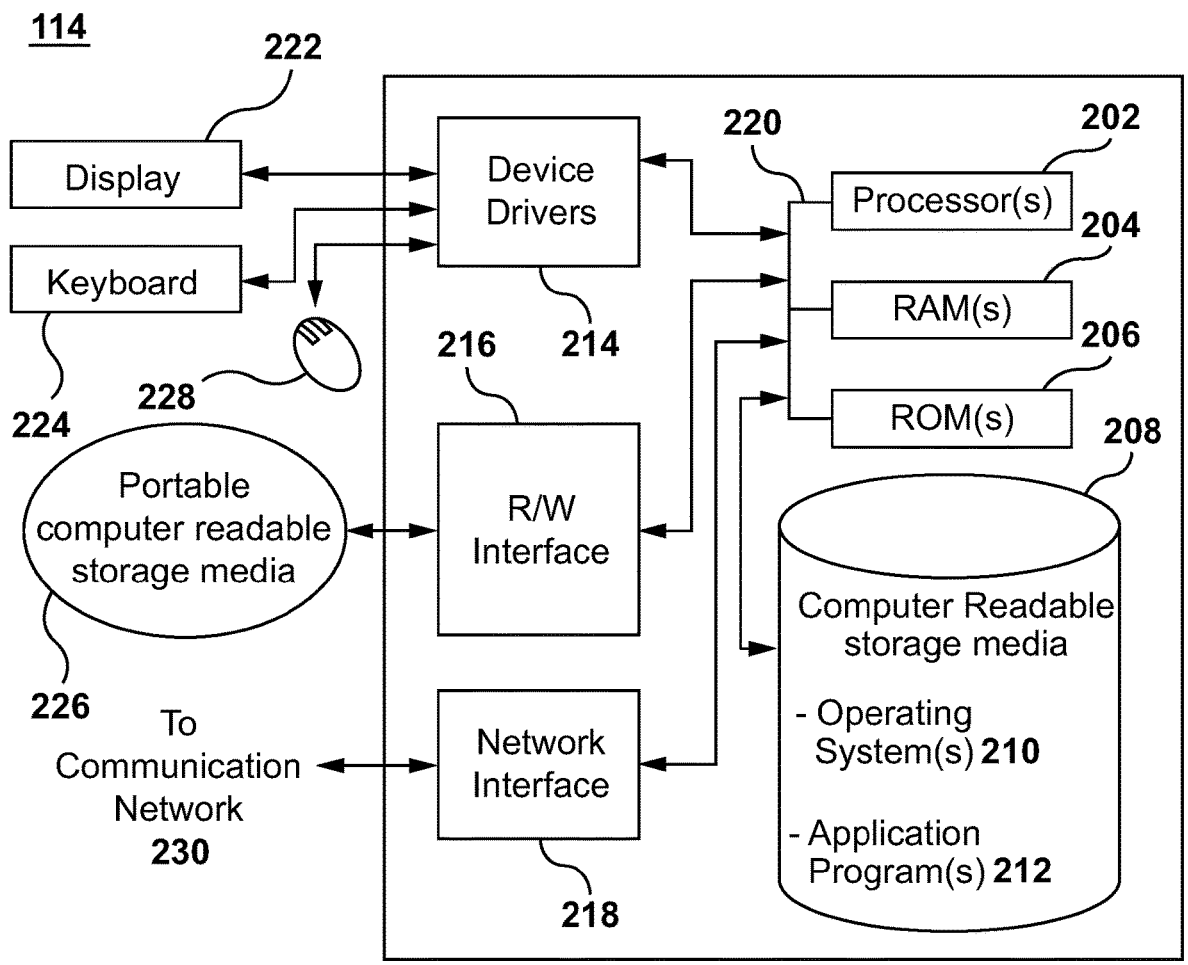
FIG. 2A depicts a high-level block diagram of components of a computer system, in accordance with various embodiments of the present disclosure.

FIG. 2A depicts a high-level block diagram of components of the computer system 114, in accordance with various embodiments of the present disclosure. It should be appreciated that FIG. 2A provides only an illustration of one implementation of the computer system 114 and does not imply any limitations with regard to the environments in which different embodiments may be implemented. Various modifications to the depicted environment are possible to implement the computer system 114 without departing from the principles presented herein. The computer system 114 may be a server, a desktop computer, a laptop computer, or any device that may be configured to implement the present technology, as understood by persons skilled in the art.

As shown, the computer system 114 employs one or more different types of processors 202, one or more computer-readable random access memories (RAMs) 204, one or more computer-readable read only memories (ROMs) 206, one or more computer-readable storage media 208, device drivers 214, a read/write (R/W) driver interface 216, a network interface 218, all interconnected over a communication fabric 220. The communication fabric 220 may be implemented by any architecture designed for communicating data and/or control information between processors (such as microprocessors, communications and network processors, etc.), system memory, peripheral devices, and any other hardware components within a system.

The processor 202 of the computer system 114 may include one or more of a CPU, an accelerator, a microprocessor, a GPU, an NPU, an ASIC, a FPGA, a dedicated logic circuitry, a dedicated artificial intelligence processor unit, or combinations thereof.

One or more operating systems 210 and one or more application programs 212 (examples of application programs may include programming instructions) are stored on one or more of computer-readable storage media 208 for execution by one or more of the processors 202 via one or more of respective RAMs 204 (which typically include a cache memory). In the illustrated embodiment, each of the computer-readable storage media 208 may be embodied as a magnetic disc storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

The R/W driver interface 216 reads from and writes to one or more portable computer-readable storage media 226. The application programs 212 may be related to the generating of the MR display of information for clinical use and stored on one or more of portable computer-readable storage media 226, read via the respective R/W driver interface 216 and loaded into the respective computer-readable storage media 208.

Further, network interface 218 may be based on a TCP/IP adapter card or wireless communication adapter (such as a wireless communication adapter using OFDMA technology). The application programs 212 on the computer system 114 may be downloaded to the computer system 114 from an external computer or an external storage device via a communication network 230 (for example, the Internet, a local area network or other wide area network or wireless network) and network interface 218. From the network interface 218, application programs 212 may be loaded onto the computer-readable storage media 208. The computer system 114 may connect to routers, firewalls, switches, gateway computers and/or edge servers of the communication network using copper wires, optical fibers, wireless transmission, and the like.

The computer system 114 may also include a display screen 222, a keyboard or keypad 224, and a computer mouse or touchpad 228. The device drivers 214 may interface with the display screen 222 for imaging, with the keyboard or the keypad 224, with the computer mouse or the touchpad 228, and/or with the display screen 222 (which may be a touch sensitive display) for alphanumeric character entry and user selections. The device drivers 214, R/W driver interface 216 and network interface 218 may comprise hardware and software (stored on the computer-readable storage media 208 and/or the ROM 206).

Figure 2B:
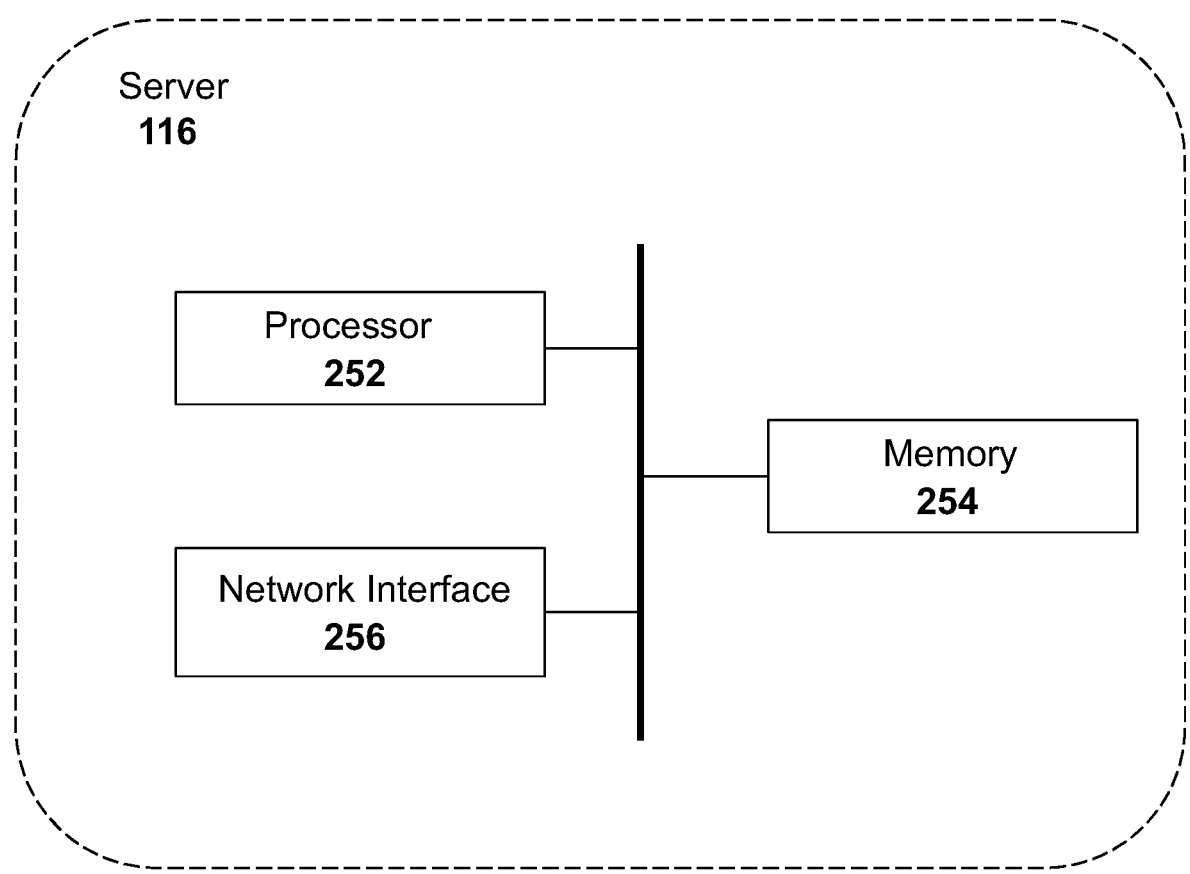
FIG. 2B depicts a high-level functional block diagram of a server, in accordance with various embodiments of the present disclosure.

FIG. 2B depicts a high-level functional block diagram of the server 116 of the system 100 of FIG. 1, in accordance with various embodiments of the present disclosure. In the depicted embodiment, the server 116 may be embodied as a physical machine (e.g., a physical server) or a virtual machine (e.g., a virtual server) that executes application programs to enable computer systems, such as the computer system 114 to communicate with the server 116. The server 116 may include a processor 252, a memory 254, and a network interface 256. It is to be noted that the server 116 may include other components which have not been illustrated for the purpose of simplicity.

The processor 252 of the server 116 may include one or more of a CPU, an accelerator, a microprocessor, a GPU, an ASIC, a FPGA, a dedicated logic circuitry, a dedicated artificial intelligence processor unit, or combinations thereof.

The memory 254 may include volatile memory (e.g., RAM) and non-volatile or non-transitory memory (e.g., a flash memory, magnetic storage, and/or a ROM). The non-transitory memory(ies) stores a platform that controls the overall operation of server 116. The platform, when executed by processor 252, implements application programs related to the generating the MR display of information for clinical use.

The network interface 256 may include one or more wireless transceivers configured for wireless communications with the communication network 230, or one or more network adaptors configured for wired communications with the communication network 230. In general, the network interface 256 may be configured to correspond with the network architecture of that is used to implement a link for communications between the server 116 and the communication network 230. In certain embodiments, the network interface 256 may be implemented in a similar manner as the network interface 218.

It is to be noted that the server 116 is shown as a standalone computer. However, the implementation of various other embodiments of the present disclosure may include any client-server model where computer systems may run a client version of the application programs related to the generating the AR and/or MR display of information for clinical use. Other examples of the server 116 may include a distributed computing system that runs the server version of the application programs related to generating AR and/or MR display of information for clinical use, a virtual machine (or virtual machines) instantiated by the infrastructure of a public or private cloud, or a cloud service provider that provides the application programs related to the generating the AR and/or MR display of information for clinical use as a service (SaaS). Such implementations or any other similar implementation should not limit the scope of the present disclosure.

Figure 3:
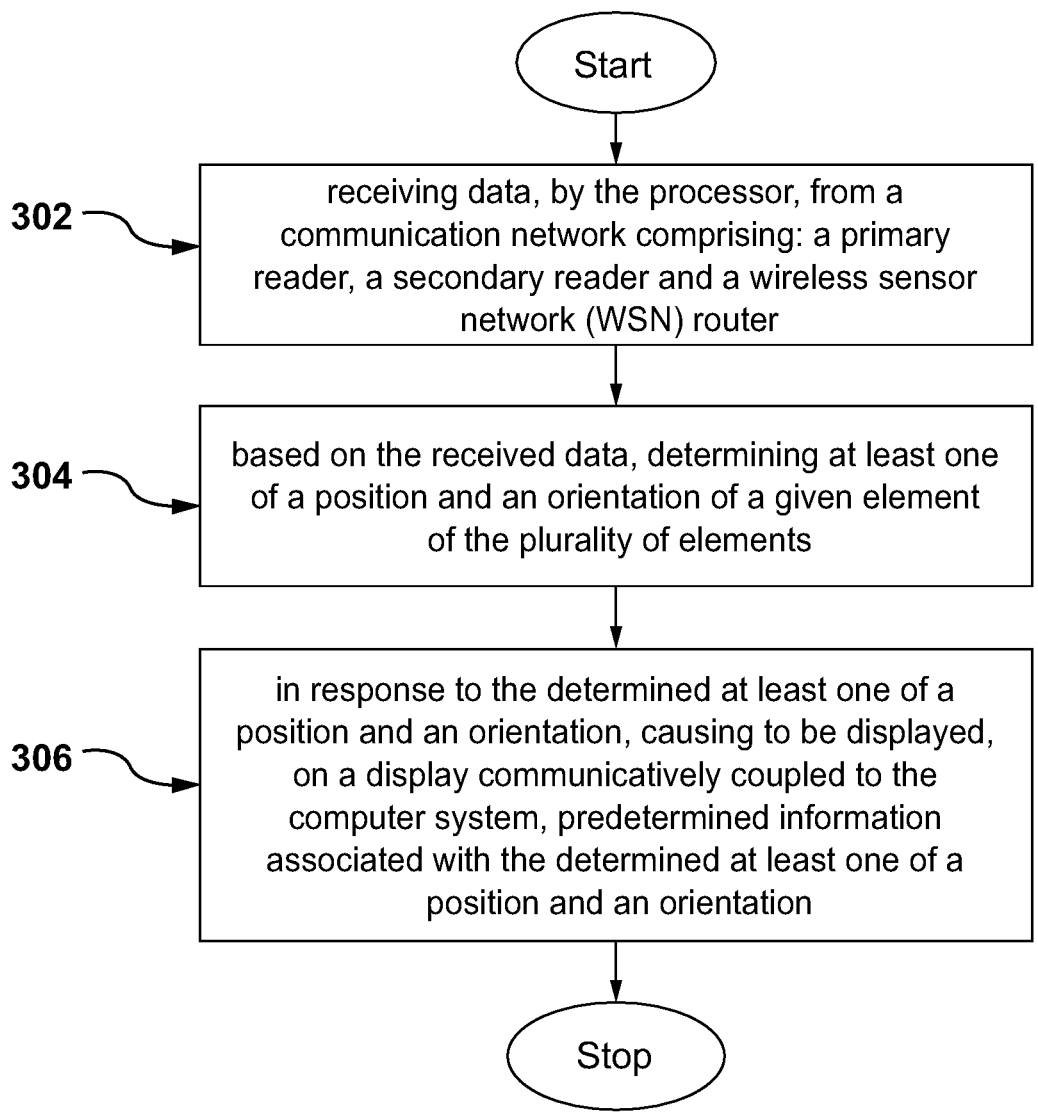
FIG. 3 illustrates a flowchart of a method implemented on the computer system of FIG. 2A for generating the display of information for clinical use, in accordance with various non-limiting embodiments of the present disclosure.

FIG. 3 illustrates a flowchart of a method 300 implemented on the system 100 for generating an MR display of information for clinical use, in accordance with various non-limiting embodiments of the present disclosure.

Step 302: Receiving Data, by the Processor, from a Communication Network Comprising: A First Reader, a Second Reader and a Wireless Sensor Network (WSN) Router The method 300 commences at step 302 where the processor 202 of computer system 114 receives the data from the communication network. The communication network comprises: the readers 110-1 and 110-2 and the WSN router 112. Referring to FIG. 1, the readers 110-1 and 110-2 may be configured to communicate with the plurality of elements 106-1, 106-2, 106-3, and 106-4 to read the received data associated with the plurality of elements 106-1, 106-2, 106-3, and 106-4.

In certain non-limiting embodiments, the plurality of elements 106-1, 106-2, 106-3, and 106-4 may be positioned at a given location relative to the medical instruments 108 and/or the patient 104. For example, the elements 106-1 and 106-2 may be attached to an operating/procedural table 109 on which the patient 104 may be lying for the purposes of the medical procedure. In other embodiments, instead of an operating/procedural table 109, the elements 106-1 and 106-2 may be attached or otherwise positioned on another type of patient support, such as a wheel chair or a bed. In some examples, the element 106-3 may be disposed on the patient 104 and the element 106-4 may be attached to the medical instrument 108. It is to be noted that the system 100 may include additional elements, which are not illustrated for the purpose of simplicity.

In some of the examples, at least some of the plurality of elements 106-1, 106-2, 106-3, and 106-4 may be RF markers (e.g., RF identification (RFID) tags) while other elements may be optical markers. In some embodiments, all of the plurality of elements 106-1, 106-2, 106-3, and 106-4 may be RF markers. In some embodiments, all of the plurality of elements 106-1, 106-2, 106-3, and 106-4 may be optical markers.

In embodiments in which at least some of the plurality of elements 106-1, 106-2, 106-3, and 106-4 are RF markers, the readers 110-1 and 110-2 may be RF readers configured to independently communicate with the plurality of elements 106-1, 106-2, 106-3, and 106-4 to receive the associated data. By way of example, the readers 110-1 and 110-2 may transmit RF signals towards the plurality of elements 106-1, 106-2, 106-3, and 106-4. In return, the plurality of elements 106-1, 106-2, 106-3, and 106-4 may reflect the associated data (such as preassigned identification).

In embodiments in which at least some of the plurality of elements 106-1, 106-2, 106-3, and 106-4 are optical markers, the readers 110-1 and 110-2 may be optical sensors configured to independently communicate with the plurality of elements 106-1, 106-2, 106-3, and 106-4 to receive the associated data. By way of example, the readers 110-1 and 110-2 may transmit light signals towards the plurality of elements 106-1, 106-2, 106-3, and 106-4 to read the associated data. In certain non-limiting embodiments, the associated data may be in the form of bar codes.

It is to be noted that a type of the elements 106-1, 106-2, 106-3, and 106-4 may depend upon requirements of the system 100 and/or the clinical use. For example, if at least some of the plurality of elements 106-1, 106-2, 106-3, and 106-4 may not remain in line of sight with the readers 110-1 and 110-2 during the medical procedure, then such elements may be RF markers and may be attached to the medical instrument 108 and the patient 104, for example. On the other hand, if some of the plurality of elements 106-1, 106-2, 106-3, and 106-4 may remain in line of sight during the medical procedure with the readers 110-1 and 110-2, then such elements may be optical markers. Such elements may be attached to the operating/procedural table 109. It is to be noted that above discussed arrangements of the plurality of elements 106-1, 106-2, 106-3, and 106-4 are for the purposes of examples only and any other arrangement may be adapted without limiting the scope of present disclosure.

As previously discussed, different medical instruments 108 to be tracked and/or tracked targets such as the patient 104 may be provided with a respective set of the plurality of elements 106-1, 106-2, 106-3, and 106-4 in different configurations. Differentiation of different medical instruments 108 and/or targets and their corresponding virtual volumes may be possible based on the specification configuration and/or orientation of the different sets of plurality of elements 106-1, 106-2, 106-3, and 106-4 relative to one another, enabling each such medical instrument 108 and/or other target to have a distinct individual identity within the system 100. The individual elements may provide data to the computer system 114 via the readers 110-1 and 110-2 and the WSN router 112, such as data related to the size and/or shape of the tracked medical instrument 108 within the system 100. The elements may also provide additional information such as a specific position on the target, such as a central point or a tip of the medical instrument 108 or a central axis of the medical instrument 108, among other information. The plurality of elements 106-1, 106-2, 106-3, and 106-4 may be tracked relative to a reference point or reference object in the operating room, such as one or more reference points on the patient 104.

In certain non-limiting embodiments, the readers 110-1 and 110-2 may include optical sensors (e.g., an infrared, LIDAR, depth and/or any other optical sensor) arranged at various locations in the surgical field. For example, optical sensor locations may include one or more of: worn by the clinicians (such as surgeon, technician, nurse, resident, or anesthesiologist), or arranged at discrete static locations such as over the surgical field, adjacent a display within the surgical field, etc.). In this embodiment, the readers 110-1 and 110-2 may be configured to scan a region of interest (ROI) based on communication with the plurality of elements 106-1, 106-2, 106-3, and 106-4. By way of example, after establishing a communication and determining a position and or an orientation of the plurality of elements 106-1, 106-2, 106-3, and 106-4, the readers 110-1 and 110-2 may scan the determined position and the orientation. In certain non-limiting embodiments, along with the data gathered from the plurality of elements 106-1, 106-2, 106-3, and 106-4, the readers 110-1 and 110-2 may provide the optical scan captured by the associated optical sensors to the computer system 114.

In certain non-limiting embodiments, the readers 110-1 and 110-2 may be configured to independently and directly communicate with the computer system 114 to forward the data gathered from the plurality of elements 106-1, 106-2, 106-3, and 106-4. Also, in certain non-limiting embodiments, the readers 110-1 and 110-2 may be configured to communicate with the computer system 114 indirectly via the WSN router 112 to forward the data gathered from the plurality of elements 106-1, 106-2, 106-3, and 106-4. Thus, the computer system 114 may be configured to receive the data from multiple sources and via multiple communication routes.

More specifically, the various communication routes can be described as: (i) the plurality of elements 106-1, 106-2, 106-3, and 106-4 to the reader 110-1 and from the reader 110-1 to the computer system 114, (ii) the plurality of elements 106-1, 106-2, 106-3, and 106-4 to the reader 110-2 and from the reader 110-2 to the computer system 114, (iii) the plurality of elements 106-1, 106-2, 106-3, and 106-4 to the reader 110-1, from the reader 110-1 to the WSN router 112, and from the WSN router 112 to the computer system 114, and (iv) the plurality of elements 106-1, 106-2, 106-3, and 106-4 to the reader 110-2, from the reader 110-2 to the WSN router 112, and from the WSN router 112 to the computer system 114.

In so doing, in case any of the communication routes are broken due to a communication link 120 break, the computer system 114 may still receive the data from another communication route which is not broken. For example, if the communication link 120 is broken between one of the readers 110-1 and 110-2 and either the WSN router 112 or the computer system 114, the computer system 114 may still receive the data gathered from the plurality of elements 106-1, 106-2, 106-3, and 106-4 via the other reader that is still communicating with the WSN router 112 and/or the computer system 114. Thus, ensuring a more accurate, stable and reliable system 100 in certain embodiments.

In certain non-limiting embodiments, the computer system 114 may be configured to determine if the data has been received from one or more of: the reader 110-1, the reader 110-2, and the WSN router 112. In other words, the computer system 114 is configured to determine which communication route the data has been received from.

Further, in certain non-limiting embodiments, the computer system 114 may be configured to interrogate the WSN router 112, the reader 110-1 and the reader 110-2 to determine if any of the communication routes or communication links from the plurality of elements 106-1, 106-2, 106-3, and 106-4 was compromised or interrupted. To do so, in certain non-limiting embodiments, the computer system 114 may be configured to transmit handshaking signals to the WSN router 112, the reader 110-1 and the reader 110-2. In return, the WSN router 112, the reader 110-1 and the reader 110-2 may transmit acknowledgment signals respectively to confirm an establishment of the respective communication routes. In case, any one of the WSN router 112, the reader 110-1 and the reader 110-2 fails to provide the acknowledgment signal, the computer system 114 may determine that the associated communication route may be compromised or interrupted. To this end, the computer system 114 may still rely on other, non-compromised communication routes to receive the data.

Figure 4:
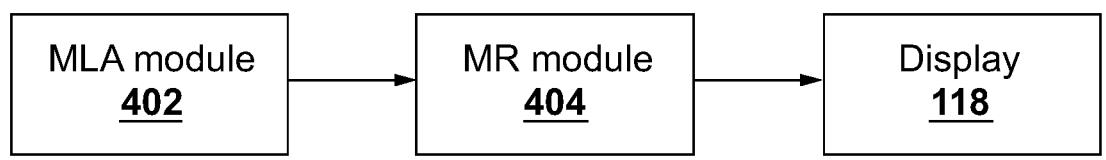
FIG. 4 illustrates at least some of the modules implemented on the computer system, in accordance with various non-limited embodiments of the present disclosure.

FIG. 4 illustrates at least some of the modules implemented on the computer system 114, in accordance with various non-limited embodiments of the present disclosure. As shown, the computer system 114 may include a machine learning algorithm (MLA) module 402 and an MR module 404. The MLA module 402 may include different trained MLA algorithms to perform different functionalities. The MR module may act as an interface for the display 118 and may control the content to be displayed on the display 118. It is to be noted that the computer system 114 may include other components and modules, however, such components and modules have been omitted from FIG. 4 for the purpose of simplicity.

In case the data has been received from more than one communication route (i.e., by more than one of the reader 110-1, the reader 110-2, and the WSN router 112), the MLA module 402 may be configured to filter the data to obtain filtered data. In other words, the MLA module 402 may be configured to filter the received data to remove the redundant data. In certain non-limiting embodiments, the filtering of data may include disregarding duplicate data based on a predetermined rule.

In certain non-limiting embodiments, the predetermined rule may include a predetermined hierarchy of communication routes. By way of example, the predetermined hierarchy of communication routes may be, in descending order: (i) the plurality of elements 106-1, 106-2, 106-3, and 106-4 to the reader 110-1 and from the reader 110-1 to the computer system 114, (ii) the plurality of elements 106-1, 106-2, 106-3, and 106-4 to the reader 110-2 and from the reader 110-2 to the computer system 114, (iii) the plurality 106-1, 106-2, 106-3, and 106-4 to the reader 110-1, from the reader 110-1 to the WSN router 112, and from the WSN router 112 to the computer system 114, and (iv) the plurality 106-1, 106-2, 106-3, and 106-4 to the reader 110-2 from the reader 110-2 to the WSN router 112, and from the WSN router 112 to the computer system 114. In other embodiments, the predetermined hierarchy of communication routes may differ.

In certain non-limiting embodiments, the MLA module 402 may be configured to disregard the duplicate data associated with the communication route which is lower in the predetermined hierarchy. In other words, the MLA module 402 may prioritize disregarding the duplicate data received from the communication route: the plurality of elements 106-1, 106-2, 106-3, and 106-4 to the reader 110-2 from the reader 110-2 to the WSN router 112, and from the WSN router 112 to the computer system 114 over other communication routes.

In certain non-limiting embodiments, the predetermined rule may be based on a predetermined hierarchy of time of transmission of the data from the plurality of elements 106-1, 106-2, 106-3, and 106-4. The most recently transmitted data may be prioritized for data processing while the data transmitted later in time may be removed by the MLA module 402 through the filtering step.

In certain non-limiting embodiments, the predetermined rule may be based on a predetermined hierarchy time of reception of the data by the computer system 114. The most recently received data may be prioritized for data processing while the data received later in time may be filtered by the MLA module 402.

The predetermined rule may be based on any other hierarchy relating to the data transmission. Any of the predetermined rules may be stored in a memory, such as the memory 254.

Step 304: Based on the Received Data, Determining at Least One of a Position and an Orientation of a Given Element of the Plurality of Elements The method 300 proceeds to step 304 where, based on the received data, the processor 202 of computer system 114 determines at least one of a position and an orientation of a given element of the plurality of elements 106-1, 106-2, 106-3, and 106-4.

In certain non-limiting embodiments, the plurality of elements 106-1, 106-2, 106-3, and 106-4 may communicate with the readers 110-1 and 110-2 to give identifiable points for tracking the patient 104, and the medical instrument 108. Based on the identifiable points, the computer system 114 may determine at least one of a position and an orientation of a given element of the plurality of elements 106-1, 106-2, 106-3, and 106-4.

In certain non-limiting embodiments, the medical/surgical instrument 108 may be defined by a grouping of at least some of the plurality of elements 106-1, 106-2, 106-3, and 106-4, which may define at least a part of a rigid body of the medical/surgical instrument 108. Thus, based on the determined position and/or the orientation of the given element of the plurality of elements 106-1, 106-2, 106-3, and 106-4, the computer system 214 may determine the position and/or orientation in of the medical instrument 108 in a 3D virtual space. The position and/or orientation of the medical instrument 108 in 3D may be tracked in six degrees of freedom (e.g., x, y, z coordinates and pitch, yaw, roll rotations), in five degrees of freedom (e.g., x, y, z, coordinate and two degrees of free rotation), but typically tracked in at least three degrees of freedom (e.g., tracking the position of the tip of the medical instrument 108 in at least x, y, z coordinates).

In a similar manner, the computer system 114 may track a position and/or orientation of the patient 104 based on the determined position and/or the orientation of the given element of the plurality of elements 106-1, 106-2, 106-3, and 106-4.

Referring to FIG. 4, in certain non-limiting embodiments, the MLA module 402 may be configured to perform a comparative analysis of the received data to ensure that the location and/or orientation of the plurality of elements 106-1, 106-2, 106-3, and 106-4 are determined in an optimized and accurate manner. The precise location may be determined by receiving the data from several communication routes and calculating the various measurements to determine position and/or orientation. In one non-limiting embodiment, the position and/or orientation of the plurality of elements 106-1, 106-2, 106-3, and 106-4 may be determined by a process referred to as triangulation. The MLA module 402 may triangulate the data and compare the readings, then use the resulting data to communicate the location to the MR module 404.

As previously noted, the plurality of elements 106-1, 106-2, 106-3, and 106-4 may be attached to the different objects (e.g., the patient 104, the medical/surgical instrument 108, and the operating/procedural table 109). In certain non-limiting embodiments, at least some of the plurality of elements 106-1, 106-2, 106-3, and 106-4, for example the elements 106-1 and 106-2, may be positioned in a fixed manner with respect to the readers 110-1 and 110-2. Such fixed elements may be used as reference points to determine a position of the other elements, such as the elements 106-3 and 106-4, that may be mobile with respect to the other elements 106-1 and 106-2 and the readers 110-1 and 110-2.

Figure 5:
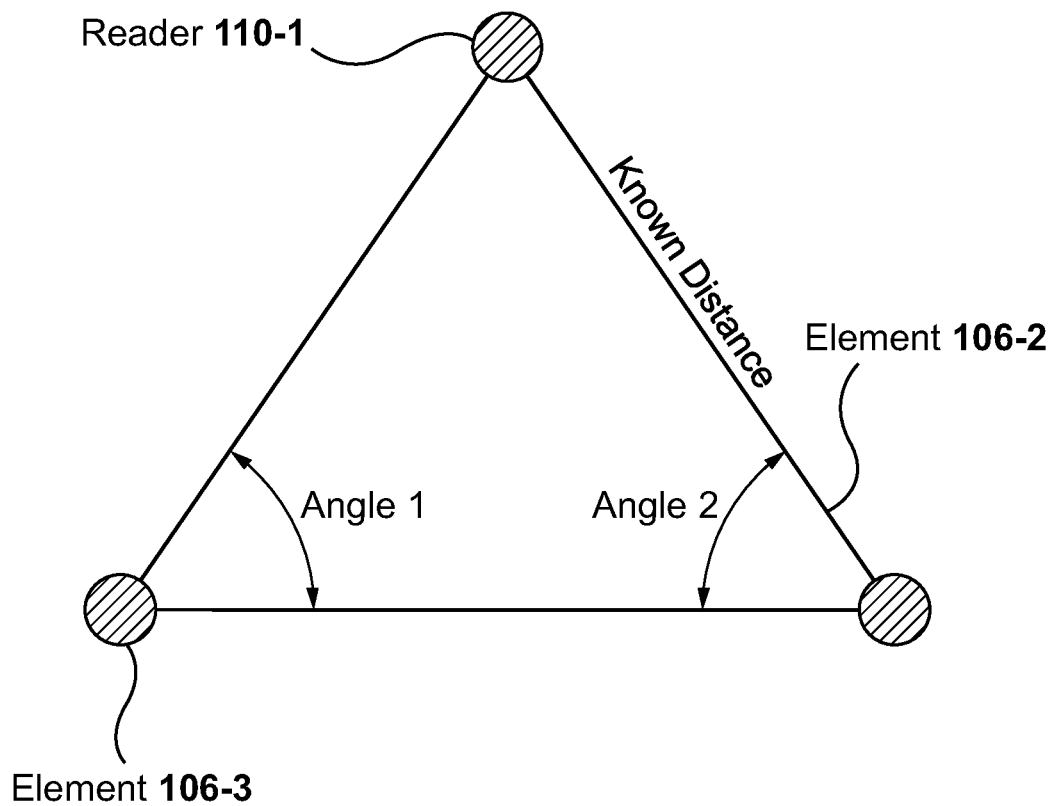
FIG. 5 illustrates a representative technique of triangulation performed by the computer system in accordance with various non-limiting embodiments of the present disclosure.

FIG. 5 illustrates a representative technique of triangulation performed by the computer system 114 in accordance with various non-limiting embodiments of the present disclosure. The triangulation approach, illustrated in FIG. 5, comprises measuring the angle of incidence of at least two elements with respect to the reader 110-1. One out of the two elements 106-2 and 106-3 may be fixed with respect to the reader 110-1 and the distance of the fixed element, such as element 106-2 may be known prior to performing the triangulation. The estimated position of the element 106-3 may correspond to the intersection of the lines defined by angle 1 and angle 2.

It is to be noted that in FIG. 5 triangulation is illustrated using two elements 106-2 and 106-3. However, in various non-limiting embodiments, more than two elements may be involved in triangulation without limiting the scope of present disclosure. Further, a similar triangulation between the plurality of elements 106-1, 106-2, 106-3, and 106-4 and the reader 110-2 may be performed by the computer system 114.

It is to be noted that in the above discussion, the MLA module 402 determines the position and/or orientation of the plurality of elements 106-1, 106-2, 106-3, and 106-4. However, in other non-limiting embodiments, the computer system 114 may rely on any suitable technique or other module to determine the position and/or orientation of the plurality of elements 106-1, 106-2, 106-3, and 106-4.

As previously noted, in addition to the data gathered from the plurality of elements 106-1, 106-2, 106-3, and 106-4, in certain non-limiting embodiments, the readers 110-1 and 110-2 may capture an optical scan of the ROI as well. The readers 110-1 and 110-2 may provide the optical scans directly to the computer system 114 or via the WSN router 112 in a similar manner as discussed above.

The computer system 114 may be configured to stitch together the optical scans to generate a three-dimensional (3D) panoramic image of the ROI. In certain non-limiting embodiments, the computer system 114 may be configured to render the 3D image onto the display 118.

In certain non-limiting embodiments, the computer system 114 may transform the optical scans into a first set of 3D color point clouds; and combine the first set of 3D color point clouds into a composite 3D color point cloud depicting the ROI. Based on the composite 3D color point cloud, the computer system 114 may then determine a position and/or orientation of the medical instrument 108 with respect to the patient 104.

The computer system 114 may additionally or alternatively compute distance data, such as in the form of a 3D point cloud output by a LIDAR sensor arranged over the operating/procedural table 109. The computer system 114 may further merge digital photographic color images with distance data to generate a substantially dimensionally accurate color map of the ROI within the operating room.

Step 306: In Response to the Determined at Least One of a Position and an Orientation, Causing to be Displayed, on a Display Communicatively Coupled to the Computer System, Predetermined Information Associated with the Determined at Least One of a Position and an Orientation The method 300 proceeds to step 306 where, in response to the determined at least one of a position and an orientation of a given element of the plurality of elements 106-1, 106-2, 106-3, and 106-4, the processor 202 of computer system 114 causes to display, on the display 118 communicatively coupled to the computer system 114, predetermined information associated with the determined at least one of a position and an orientation.

The predetermined information may include but not limited to augmented still/video images, medical procedure guidance, navigation menu, eye fatigue indicator, surgeon's profile, annotations or the like, details of which are discussed below.

Referring to FIG. 4, in certain non-limiting embodiments, after determining the position and/or orientation of the given element of the plurality of elements 106-1, 106-2, 106-3, and 106-4, the MLA module 402 may be configured to provide the position and/or orientation to the MR module 404. The position and the orientation may act as a trigger for the MR module 404 to initiate and control the predetermined information to be displayed on the display 118.

As previously discussed, the system 100 may include the display 118. The display 118 may be used during a medical procedure to project or display the predetermined information during the medical procedure to augment the surgeon's vision. The display of predetermined information may be based on the determined position and the orientation of a given element of the plurality of elements 106-1, 106-2, 106-3, and 106-4. The MR module 404 may be based on MARGE™ platform, for example. MARGE™ platform is an MR content authoring and delivery platform that may be incorporated in the MR module 404. The MARGE™ platform may assist the MR module 404 to act as a platform between the MLA module 402 and the display 118.

In some non-limiting embodiments, the computer readable storage media 208 may be configured to store various still/video images to be delivered to the display 118. For example, the images may include information useful to the clinician for the medical procedure and setup. In other non-limiting embodiments, the memory 254 associated with the server 116 may be configured to store the various still/video images to be delivered to the display 118, such as for the pre-operation medical procedure and setup. In any case, the MLA module 402 may be configured to fetch the still/video images either from the computer readable storage media 208 or from the memory 254.

In certain non-limiting embodiments, the system 100 may include additional cameras (not illustrated) to capture still/video images of the at least a portion of the patient 104. In embodiments in which the display 118 is a wearable device, such cameras may be integrated with the wearable device. In other embodiments, such cameras may be located near to the patient 104, or be positioned relative to the patient to capture images of the patient. The computer system 114 may be configured to receive the still/video images captured by the additional cameras, such as, in the form of optical scans as previously discussed. The computer system 114 may be configured to stitch together the optical scans to generate a three-dimensional (3D) panoramic image.

The MLA module 402 may be configured to provide all the still/video images fetched from the computer readable storage media 208 or from the memory 254 or captured by the additional cameras to the MR module 404. In response to the determined position and/or the orientation of a given element of the plurality of elements 106-1, 106-2, 106-3, and 106-4, the MR module 402 may be configured to augment virtual objects over the still/video images.

The MR module 404 may be configured to transmit the augmented still/video images to the display 118 at the determined position and/or the orientation of a given element of the plurality of elements 106-1, 106-2, 106-3, and 106-4 and may integrate it using multi-sensor data fusion relative to the surrounding data collected from the sensors, such as sensors on the wearable device.

In certain non-limiting embodiments, the MR module 404 may be configured to determine a navigational guide, along with actionable digital elements such as a digital button to be displayed on the display 118 to assist the surgeon 102 to perform certain medical procedures such as inserting prostheses, implants, guides, anchorage devices and other surgical devices which would be part of the medical procedure. The navigational guide along with the actionable digital elements may improve the interaction control of the surgeon 102 over the display 118. It is to be noted that the MR virtualizations may be streamed at the desired position and orientation via server 116, cloud services, or the like without limiting the scope of present disclosure.

In certain non-limiting embodiments, the MR module 404 may provide an ability to incorporate spatial gesture recognition. The spatial gestures may include but are not limited to movement of eyes, head, arms, hands etc. It is to be noted that the tracking of the spatial gesture may be performed by any suitable technique, for example, computer vision. Prior to the transmitting the augmented still/video images, the MR module 404 may provide a visual pointer displayed on the display 118. The visual pointer may be moved (through spatial gesture recognition) to the desirable spatial viewpoint at which the augmented still/video images may be streamed.

In certain non-limiting embodiments, the navigational guide may have a navigation menu that may allow the surgeon 102 to properly select the image related to the intended medical/surgical procedure for example, via spatial gesture movement. The navigation menu may reflect gamification functionality which may engage the surgeon 102 during the medical procedure. Such functionality may further include aspects relating to surgical ergonomics that may reduce discomfort and mitigate negative downstream consequences.

In certain non-limiting embodiments, the MR module 404 may provide an indicator on the display 118. The indicator may provide an indication of eye fatigue warning. The indicator may comprise a power bar-type meter representation which may be located on the display 118 in the field of view of the surgeon 102. The power in the bar may be determined by eye-level postural deviations from normal values associated with the given surgeon 102 or typical base line values.

In certain non-limiting embodiments, the computer system 114 may allow a registration of the physician/surgeon's profile on a network such as the server 116. The registration may include registering physicians/surgeons in an online application by saving their credentials and preferences in a database, such as the memory 254. The registration process may assist the MR module 404 to display a physician's/surgeon's preferences relating to the predetermined information such as sizes, angles and views of images and text, medical/surgical preferences and preferred medical/surgical instruments 108 (e.g. tools that contain sensors). The physician/surgeon preferences may be manually input or be determined by the AI module. In another example, the surgeon's profile would allow for providing rights and privileges, authorization, and capturing time stamps.

In certain non-limiting embodiments, the MR module 404 may provide annotating the displayed image. The physician/surgeon 102 may annotate virtual or real objects on the display 118 for example, the physician/surgeon may change the angle of a rod insertion relative to a reference angle as provided by the MLA module 402. By fixing annotations to a spatial location, the MR module 404 may enable the surgeon to annotate their MR experience in the virtual space. An annotation displayed in the virtual space remains readable at all viewing angles and distances.

The process of annotating may allow the physician/surgeon 102 to quickly define a placement using a spatial gesture input, providing a benefit of localization and data accessibility. In certain non-limiting embodiments, the MR module 404 may provide annotating a procedure, or an object by determining where the annotation is located in the physical environment and by adding a visual gesture recognizer to the view.

Annotation may also provide an overlay of a surgical plan allowing for mark-up to represent any deviation that the surgeon 102 wishes to introduce relative to the best practice. In certain non-limiting embodiments, the MR module 404 may provide a remote assistance feature, though which the physician/surgeon 102 may consult with a knowledge-based individual for further assistance in the medical procedure.

Figure 6:
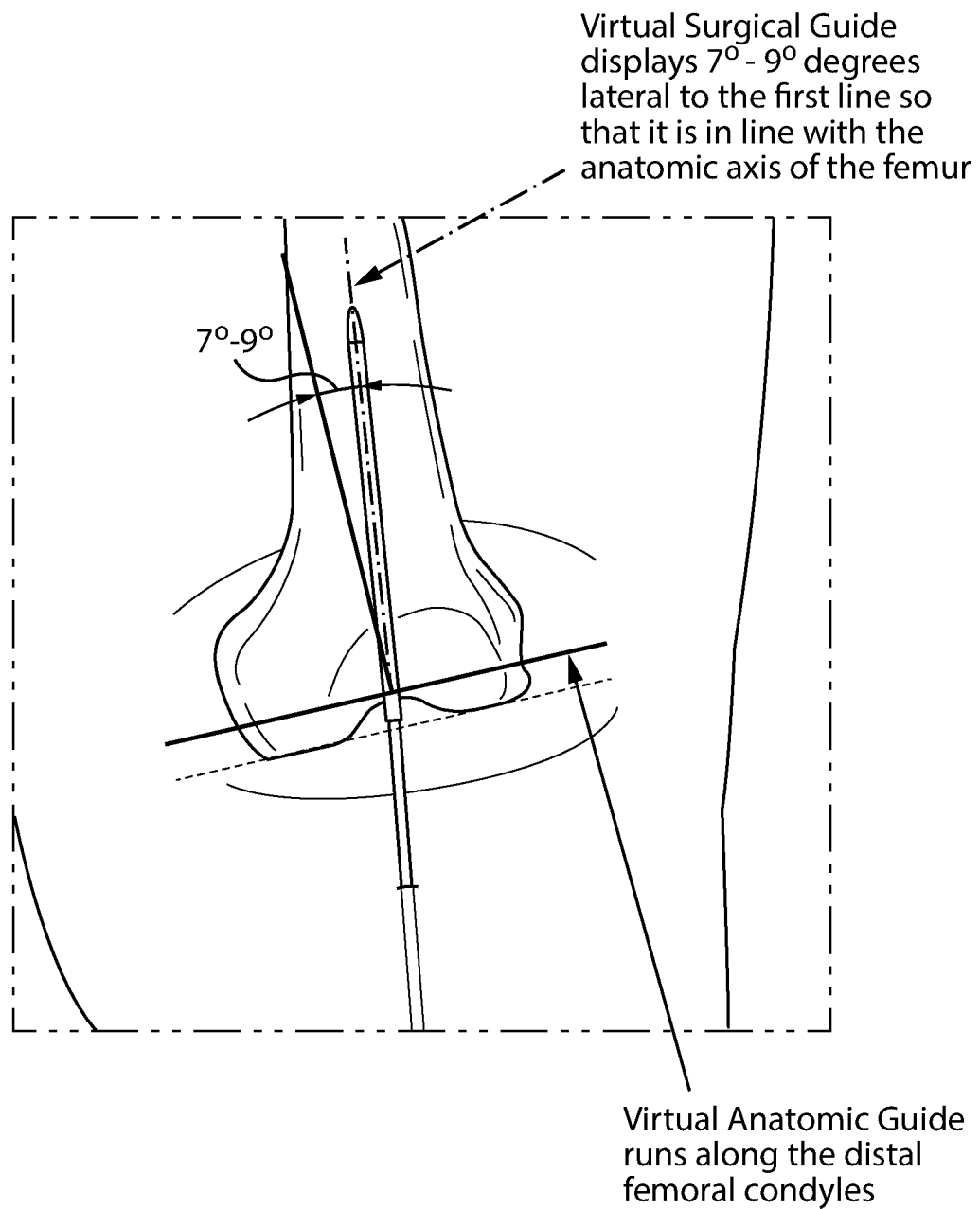
FIG. 6 illustrates a representative display depicting predetermined information overlaid over a patient's body part in accordance with various non-limiting embodiments of the present disclosure.

FIG. 6 illustrates a representative display depicting predetermined information overlaid over a patient's body part in accordance with various non-limiting embodiments of the present disclosure. FIG. 6 illustrates an insertion point and an orientation of a retrograde nail to be inserted in the patient 104. A virtual surgical plan is overlaid over the corresponding anatomy of the patient 104 in real-time. An optimal location and orientation of the retrograde nail is indicated as the predetermined information and/or the surgical plan.

Figure 7:
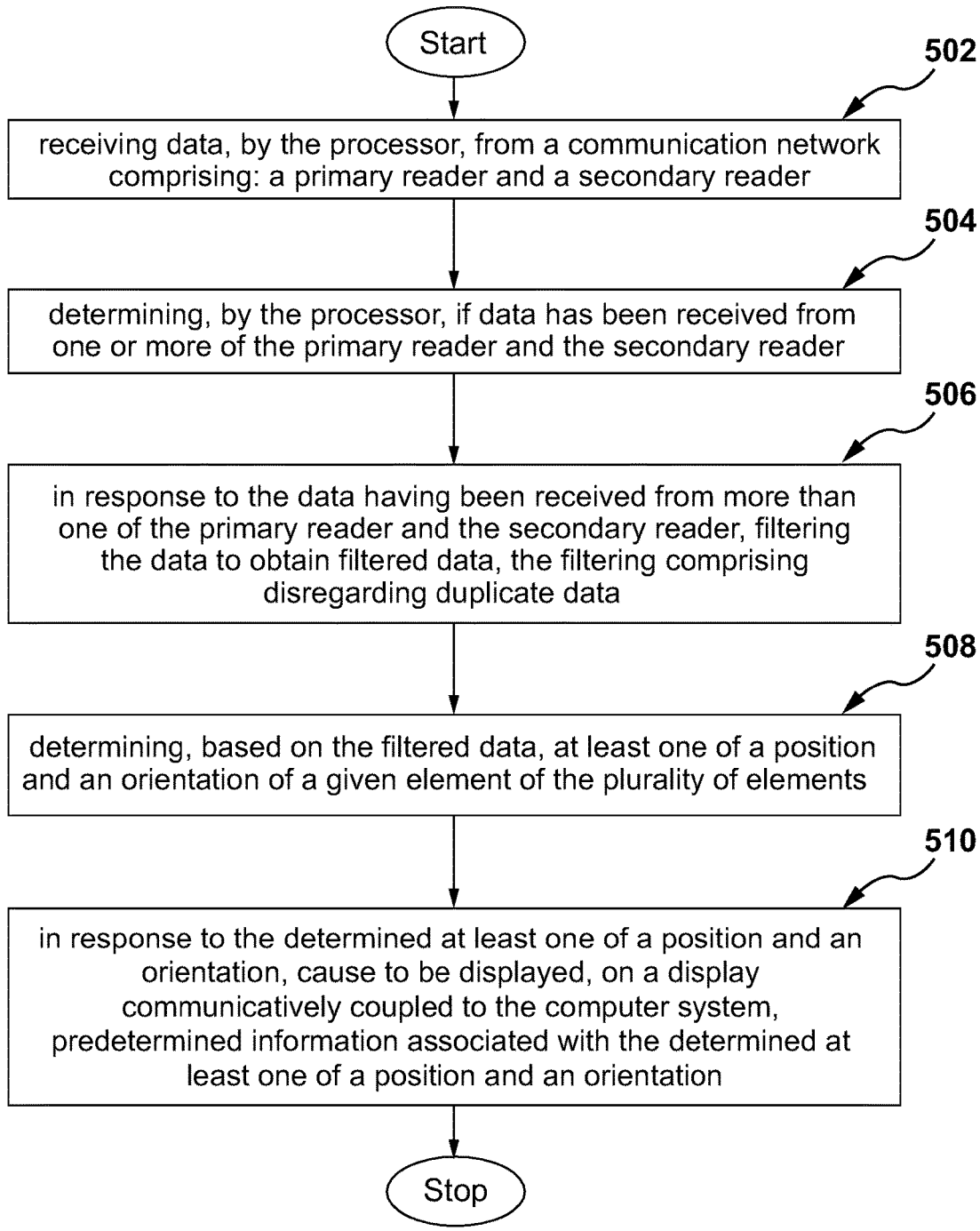
FIG. 7 illustrates a flowchart of a method implemented on the computer system of FIG. 2A for generating the display of information for clinical use, in accordance with various alternative non-limiting embodiments of the present disclosure.

FIG. 7 illustrates a flowchart of another method 500, according to aspects and embodiments of the present technology. The method 500 may be implemented on the system 100 for generating a MR display of information for clinical use, in accordance with various non-limiting embodiments of the present disclosure.

Step 502: Receiving Data, by the Processor, from a Communication Network Comprising: A First Reader and a Second Reader The method 500 commences at step 502 where the processor 202 of the computer system 114 receives the data from the communication network. The communication network comprises readers 110-1 and 110-2. As previously noted, the reader 110-1 is communicatively coupled to, and configured to receive data from, each element of a plurality of elements 106-1, 106-2, 106-3, and 106-4, each element positioned at a given location relative to an object at a clinical site. Similarly, the reader 110-2 is communicatively coupled to, and configured to receive data from, each element of the plurality of elements 106-1, 106-2, 106-3, and 106-4, each element positioned at a given location relative to an object at a clinical site. Optionally, the communication network may also include the WSN router 112. The processor 202 of computer system 114 may receive the data from a WSN router 112 in addition to the readers 110-1 and 110-2. The WSN router 112 may be communicatively coupled to, and configured to receive data from, each of the readers 110-1 and 110-2.

Step 504: Determining, by the Processor, if Data has been Received from One or More of the First Reader, and the Second Reader The method 500 proceeds to step 504 where the processor 202 of computer system 114 determines if the data has been received from one or more of the readers 110-1 and 110-2. Optionally, the processor 202 of the computer system 114 may determine if the data has been received from the WSN router 112 as well.

Step 506: In Response to the Data Having been Received from More than One of the First Reader and the Second Reader, Filtering the Data to Obtain Filtered Data, the Filtering Comprising Disregarding Duplicate Data The method 500 proceeds to step 506 where in response to the data having been received from more than one of the readers 110-1 and 110-2, the processor 202 of the computer system 114 may be configured to filter the data to obtain filtered data. As previously noted, the step of filtering comprises disregarding duplicate data. As previously noted, in embodiments in which the data has been received from more than one of the reader 110-1, the reader 110-2, the MLA module 402 may be configured to perform filtering the data to obtain filtered data. In other words, the MLA module 402 may be configured to perform filtering of the received data to remove the redundant data. In certain non-limiting embodiments, the filtering of data may include disregarding duplicate data based on a predetermined rule (discussed previously).

Step 508: Determining, Based on the Filtered Data, at Least One of a Position and an Orientation of a Given Element of the Plurality of Elements The method 500 proceeds to step 508 where based on the filtered data, the processor 202 of computer system 114 determines at least one of a position and an orientation of a given element of the plurality of elements 106-1, 106-2, 106-3, and 106-4. It is to be noted that the process of determining at least one of the position and the orientation of the given element of the plurality of elements 106-1, 106-2, 106-3, and 106-4 may performed in a similar manner as previously discussed with respect to step 304 of the method 300.

Step 510: In Response to the Determined at Least One of a Position and an Orientation, Cause to be Displayed, on a Display Communicatively Coupled to the Computer System, Predetermined Information Associated with the Determined at Least One of a Position and an Orientation The method 500 proceeds to step 510 where in response to the determined at least one of the position and the orientation of a given element of the plurality of elements 106-1, 106-2, 106-3, and 106-4, the processor 202 of computer system 114 causes to display, on the display 118 communicatively coupled to the computer system 114, predetermined information associated with the determined at least one of a position and an orientation. It is to be noted that the process of displaying on the display 118 may performed in a similar manner as previously discussed with respect to step 306 of the method 300. By virtue of multiple routes to transmit the data from the plurality of elements 106-1, 106-2, 106-3, and 106-4 to the computer system 114, the system 100 provides stable, accurate and reliable localization of the MR content, in certain embodiments.

Network redundancy (i.e., multiple routes) adds additional instances of network components and lines of communication to ensure data availability and decrease a risk of failure along the critical data routes. When one communication route is unavailable, an alternate communication route may be instantly deployed to ensure minimal downtime and continuity of network services thus improving the reliability. By adding targeted complexity, the system 100 reduces the probability that a failure will take the system down. In addition to network redundancy, the system 100 also provide data redundancy, thereby increasing the accuracy of the data.

It is to be understood that the operations and functionality of system 100, constituent components, and associated processes may be achieved by any one or more of hardware-based, software-based, and firmware-based elements. Such operational alternatives do not, in any way, limit the scope of the present disclosure.

It will also be understood that, although the embodiments presented herein have been described with reference to specific features and structures, it is clear that various modifications and combinations may be made without departing from such disclosures. The specification and drawings are, accordingly, to be regarded simply as an illustration of the discussed implementations or embodiments and their principles as defined by the appended claims, and are contemplated to cover any and all modifications, variations, combinations or equivalents that fall within the scope of the present disclosure.

What is claimed is:

1. A method for displaying predetermined information for clinical use, the method executable by a processor of a computer system, the method comprising: receiving data, by the processor, from a communication network comprising: a first reader, a second reader and a wireless sensor network (WSN) router: the first reader being communicatively coupled to, and configured to receive data from, each element of a plurality of elements, each element positioned at a given location relative to an object at a clinical site; the second reader being communicatively coupled to, and configured to receive data from, each element of the plurality of elements; the WSN router communicatively coupled to, and configured to receive data from, each of the first reader and the second reader; based on the received data, determining at least one of a position and an orientation of a given element of the plurality of elements; in response to the determined at least one of the position and the orientation, causing to be displayed, on a display communicatively coupled to the computer system, predetermined information associated with the determined at least one of the position and the orientation.

2. The method of claim 1 further comprising:
determining if the data has been received from more than one of: the first reader, the second reader and the WSN router;
in response to the data having been received from more than one of the first reader, the second reader and the WSN router, filtering the data to obtain filtered data, the filtering comprising disregarding duplicate data based on a predetermined rule, the determining the at least one of the position and the orientation being based on the filtered data.

3. The method of claim 2, wherein determining if the data was received from more than one of the first reader, the second reader and the WSN router comprises the processor interrogating the first reader, the second reader and the wireless sensor network (WSN) router to determine if any one of communication routes between the plurality of elements and the computer system was compromised.

4. The method of claim 2, wherein the predetermined rule comprises one of: a predetermined hierarchy of communication routes between the plurality of elements and the computer system, a predetermined hierarchy of time of transmission of the data; and a predetermined hierarchy of time of reception of the data by the computer system.

5. The method of claim 1, wherein the object is one or more of: a patient, a medical/surgical instrument, and operating/procedural table.

6. The method of claim 1, wherein determining at least one of the position and the orientation of the given element of the plurality of elements comprises triangulation.

7. The method of claim 6, wherein the triangulation is performed by computing angles of incidences between the plurality of elements and the first reader and the second reader.

8. The method of claim 1, wherein the display is a fixed display or is part of a wearable device.

9. The method of claim 1, wherein the predetermined information is one or more of: an augmented image, a medical procedure guidance, a navigation menu, an eye fatigue indicator, a user's profile, and an annotation.

10. The method of claim 1, wherein displayed information comprises an actionable digital element, based on an input received from a user, the actionable digital element is configured to display of further information associated with the predetermined information.

11. The method of claim 1, wherein the processor is configured to retrieve the predetermined information from a memory of the computer system.

12. The method of claim 1, wherein the predetermined information which is displayed is based on a user's profile.

13. The method of claim 1, further comprising tracking user's eye, head or arm movement for interaction with the display.

14. The method of claim 1, wherein the plurality of elements are radio frequency based elements.

15. The method of claim 1, wherein the plurality of elements are optical based elements.

16. A system for displaying predetermined information for clinical use, the system comprising a communication network including: a plurality of elements having data stored therein and positioned at a given location relative to an object at a clinical site; a first reader and a second reader, each of the first reader and the second reader communicatively coupled to each element of the plurality of elements and configured to receive the data from each element of the plurality of elements and transmit the data to a computer system; a wireless sensor network (WSN) router configured to receive the data from the first reader and the second reader and transmit the data to the computer system; the computer system being independently communicatively coupleable with each of the first reader, the second reader and the WSN router for receiving the transmitted data independently from each of the first reader, the second reader and the WSN router; wherein the computer system is configured to execute a method comprising: receiving data from the communication network; based on the received data, determining at least one of a position and an orientation of a given element of the plurality of elements; in response to the at least one of the determined position and the orientation, causing display, on a display communicatively coupled to the computer system, predetermined information associated with the determined the at least one of the determined position and the orientation.

17. The system of claim 16, wherein the plurality of elements are radio frequency based elements.

18. The system of claim 16, wherein the plurality of elements are optical based elements.

19. A method for displaying predetermined information for clinical use, the method executable by a processor of a computer system, the method comprising: receiving data, by the processor, from a communication network comprising: a first reader and a second reader: the first reader being communicatively coupled to, and configured to receive data from, each element of a plurality of elements, each element positioned at a given location relative to an object at a clinical site; the second reader being communicatively coupled to, and configured to receive data from, each element of the plurality of elements, each element positioned at a given location relative to the object at the clinical site; determining, by the processor, if the data has been received from one or more of the first reader and the second reader; in response to the data having been received from more than one of the first reader and the second reader, filtering the data to obtain filtered data, the filtering comprising disregarding duplicate data; determining, based on the filtered data, at least one of a position and an orientation of a given element of the plurality of elements; in response to the determined at least one of the position and the orientation, cause to be displayed, on a display communicatively coupled to the computer system, predetermined information associated with the determined at least one of the position and the orientation.

20. The method of claim 19, wherein the communication network further comprises a wireless sensor network (WSN) router, the WSN router communicatively coupled to, and configured to receive data from, each of the first reader and the second reader, the method further comprising receiving data from the WSN router.

\* \* \* \* \*